(12) United States Patent
Keren et al.

(10) Patent No.: US 7,704,702 B2
(45) Date of Patent: *Apr. 27, 2010

(54) TEST STRIP FOR LATERAL FLOW ASSAYS

(75) Inventors: Tomer Keren, Rishon Le Zion (IL); Oren Shraga Dwir, Rehovot (IL)

(73) Assignee: Inverness Medical Switzerland GmbH, Zug (CH)

( * ) Notice: Subject to any disclaimer, the term of this patent is extended or adjusted under 35 U.S.C. 154(b) by 305 days.

This patent is subject to a terminal disclaimer.

(21) Appl. No.: 11/502,256

(22) Filed: Aug. 10, 2006

(65) Prior Publication Data

US 2008/0038759 A1    Feb. 14, 2008

(51) Int. Cl.
 *G01N 33/543*    (2006.01)

(52) U.S. Cl. ........................ 435/7.4; 436/158; 436/528; 436/538; 436/541; 436/518; 436/808; 436/810; 435/4; 435/7.1; 435/287.1; 435/287.2; 435/287.8; 435/287.9; 435/7.72; 435/805

(58) Field of Classification Search ................ 436/158, 436/528, 538, 541, 808, 810, 518; 435/4, 435/7.1, 287.1, 287.2, 287.8, 287.9, 805, 435/7.4, 7.72

See application file for complete search history.

(56) References Cited

U.S. PATENT DOCUMENTS

| | | | |
|---|---|---|---|
| 4,499,185 A | 2/1985 | Skjold et al. | |
| 4,859,612 A | 8/1989 | Cole et al. | |
| 5,200,317 A | 4/1993 | Georgevich | |
| 5,360,595 A | 11/1994 | Bell et al. | |
| 5,622,871 A | 4/1997 | May et al. | |
| 6,472,226 B1 * | 10/2002 | Barradine et al. | ........... 436/518 |
| 6,512,100 B1 | 1/2003 | Johnson et al. | |
| 6,607,896 B1 | 8/2003 | Millar et al. | |
| 6,667,161 B1 | 12/2003 | Johnson et al. | |
| 6,753,189 B1 | 6/2004 | Narahara et al. | |

(Continued)

FOREIGN PATENT DOCUMENTS

DE    196 32 432 A1    2/1998

(Continued)

OTHER PUBLICATIONS

Spiegel et al. "Diagnosis of Bacterial Vaginosis by Direct Gram Stain of Vaginal Fluid." *Journal of Clinical Microbiology*. vol. 18. No. 1. Jul. 1983. pp. 170-177.

(Continued)

*Primary Examiner*—Bao-Thuy L Nguyen
(74) *Attorney, Agent, or Firm*—Foley Hoag LLP

(57) ABSTRACT

A test strip configured for the detection of an analyte in a fluid sample and methods for manufacturing and for using the same. The test strip comprises a first flow matrix and a second flow matrix sequentially arranged to form an interface therebetween. The first flow matrix comprises a detection composition movably bound thereto, wherein the detection composition when exposed to the analyte produces at least one detectable product and wherein the first and second solid matrices are selected so as to accumulate the at least one detectable product at the interface between the two matrices, when the fluid sample travels from the first flow matrix to the second flow matrix.

19 Claims, 5 Drawing Sheets

U.S. PATENT DOCUMENTS

| | | | |
|---|---|---|---|
| 7,256,000 B2* | 8/2007 | Goertz et al. | 435/7.1 |
| 7,591,978 B2 | 9/2009 | Dwir et al. | |
| 2002/0127614 A1 | 9/2002 | Barradine et al. | |
| 2003/0162240 A1 | 8/2003 | Johnson et al. | |
| 2003/0181691 A1 | 9/2003 | Johnson et al. | |

FOREIGN PATENT DOCUMENTS

| | | |
|---|---|---|
| EP | 1 657 550 A1 | 5/2006 |
| WO | WO 88/05912 | 8/1988 |
| WO | WO00/55354 A3 | 9/2000 |

OTHER PUBLICATIONS

Nugent et al. "Reliability of Diagnosing Bacterial Vaginosis is Improved by a Standardized Method of Gram Stain Interpretation." *Journal of Clinical Microbiology*. vol. 29. No. 2. Feb. 1991. pp. 297-301.

Sobel. "Vaginitis". *The New England Journal of Medicine*. vol. 337. No. 26. Dec. 25, 1997. pp. 1896-1903.

Briselden et al. "Sialidases (Neuraminidases) in Bacterial Vaginosis and Bacterial Vaginosis-Associated Microflora." *Journal of Clinical Microbiology*. vol. 30. No. 3. Mar. 1992. pp. 663-666.

McGregor et al. "Bacterial Vaginosis is Associated with Prematurity and Vaginal Fluid Mucinase and Sialidase: Results of a Controlled Trial of Topical Clindamycin Cream." *Am J Obstetrics Gynecology*. vol. 170. No. 4. Apr. 1994. pp. 1048-1060.

Wiggins et al. "Mucinases and Sialidases: Their Role in the Pathogenesis of Sexually Transmitted Infections in the Female Genital Tract." *Sexually Transmitted Infections* (STI Online). vol. 77. 2001. pp. 402-408.

Olmsted et al. "Glycosidase and Proteinase Activity of Anaerobic Gram-Negative Bacteria Isolated from Women with Bacterial Vaginosis." *Sexually Transmitted Diseases*. vol. 30. No. 3. Mar. 2003. pp. 257-261.

Smayevsky et al. "Vaginal Microflora Associated with Bacterial Vaginosis in Nonpregnant Women: Reliability of Sialidase Detection." *Infectious Diseases in Obstetrics and Gynecology*. vol. 9. 2001. pp. 17-22.

Wiggins et al. "Use of 5-Bromo-4-Chloro-3-Indolyl-α -D-N-Acetylneuraminic Acid in a Novel Spot Test to Identify Sialidase Activity in Vaginal Swabs from Women with Bacterial Vaginosis." *Journal of Clinical Microbiology*. vol. 38. No. 8. Aug. 2000. pp. 3096-3097.

Bradshaw et al. "Evaluation of a Point-of-Care Test, BVBlue, and Clinical and Laboratory Criteria for Diagnosis of Bacterial Vaginosis." *Journal of Clinical Microbiology*. vol. 43. No. 3. Mar. 2005. pp. 1304-1308.

Brochure for BVBlue Test.

Fujii et al. "X-Neu5Ac: A Novel Substrate for Chromogenic Assay of Neuraminidase Activity in Bacterial Expression Systems." *Bioorganic & Medicinal Chemistry*. vol. 1. No. 2. 2003. pp. 147-149.

Myziuk et al. "BVBlue Test for Diagnosis of Bacterial Vaginosis." *Journal of Clinical Microbiology*. vol. 41. No. 5. May 2003. pp. 1925-1928.

Gossrau et al. "Azoindoxyl Methods for the Investigation of Hydrolases." *Histochemistry*. No. 57. 1978. pp. 323-342.

Gossrau et al. "5-Brom-3-indolyl-α-ketoside of 5-N-Acetyl-D-neuraminic Acid a New Substrate for the Light and Electron Microscopic Demonstration of Mammalian Neuraminidase." *Histochemistry*. No. 53. 1977. pp. 189-192.

Gossrau et al. "Tetrazolium Methods for the Histochemical Investigation of Hydrolases." *Histochemistry*. No. 58. 1978. pp. 203-218.

Gossrau et al. "Indoxyl Alfa-D-Galactoside as the Temporarily Last Substrate for Glycosidase Histochemistry. The Present State of the Art in Histochemical Glycosidase Research Using Indoxyl Glycosidas." *Folia Histochemica et Cytobiologica*. vol. 28. No. 3. 1990. pp. 129-144.

Lojda et al. "Enzyme Histochemistry. A Laboratory Manual." Springer-Verlag. 1979. pp. 138-139.

International Search Report mailed Nov. 20, 2007 for PCT/IL2007/000992.

* cited by examiner

AP  0     1    1:10 1:100

1= 0.0375 units per test

TEST STRIP FOR LATERAL FLOW ASSAYS

BACKGROUND OF THE INVENTION

1. Field of the Invention

The present invention generally relates to test devices for rapid assays and more specifically to device and method for a novel lateral-flow assay.

2. Discussion of the Related Art

Rapid diagnostic in vitro assays for detecting the presence of biological compounds have become routine for a variety of applications including medical diagnosis, environmental monitoring, forensic toxicology and food pathogen testing. The ever-increasing demand for new, low-cost and sensitive rapid assays have generated many new developments in this field over recent years. However there is still a continuous need for new and improved detection methods and devices of higher sensitivity and of lower cost. In particular, there is a great demand for low-cost point-of-care clinical diagnostics kits that can be used by untrained persons.

One popular format for performing one-step rapid assays is the lateral flow assay technology where a sample is applied at one end of a test strip pre-treated with assay specific reagents. The sample is drawn along the strip by capillary action, traveling through an indicator zone where the appearance of a visible, or otherwise detectable signal, indicates the presence of the analyte in the sample. The indicator zone typically comprises a member of a specific binding pair immobilized to the strip in a defined area, typically a line. The strip may further comprise a labeling zone, located downstream the sample application zone, provided with a labeling substance. The lateral flow assay is carried out by applying the sample suspected of containing the analyte at the sample receiving end and allowing it to travel along the strip by capillary action, to pick up the label compound when present, and further downstream to be captured and concentrated at the detection/capture zone. There exist many variations of this basic structure, regarding the number and nature of the immobilized, labeling and other substances located along the strip and their interaction with the analyte, as well as to the nature and formation of the detectable signal. For example, the detectable signal does not necessarily result from a direct interaction between the immobilized substance and the analyte but, depending on the specific assay and strip structure, may result from indirect interaction with a secondary product that is formed upstream of the immobilized substance and whose production requires the presence of the analyte. In accordance with other variations, the immobilized reagent may serve to capture un-reacted upstream reagents, for example unbound label reagent, while the detection zone is located downstream the capture zone. However, in most cases, prior art lateral flow strips include at least one pre-immobilized reagent.

The present invention provides a novel strip for lateral flow assays where all the detection reactants are movably bound to the strip and wherein the capture zone is formed at the interface between two sequentially ordered flow matrices of different characteristics.

In particular, the strip of the present invention is suitable for, but is not limited to, the detection of enzymes, or enzymes substrates, in bodily fluids.

SUMMARY OF THE PRESENT INVENTION

One aspect of the present invention is a test strip for the detection of an analyte in a fluid sample, which is devoid of pre-immobilized reagents. The strip comprises a first and a second flow matrices sequentially arranged to form a junction therebetween, wherein the first flow matrix comprises a detection composition movably bound thereto and wherein at least one component of the detection composition may be pre-deposited on the first matrix in a dry form. The detection composition in selected so as to produce at least one detectable product upon exposure to the analyte. The first and second solid matrices are selected so as to accumulate the at least one detectable product at the junction between the matrices, when the fluid sample travels from the first matrix to the second matrix. The first matrix is of higher porosity than the second matrix to allow higher permeation rate of the detectable product through the first matrix. Preferably, the components of the detecting composition are solvable in the sample fluid while the at least one detectable product is insoluble in the sample fluid. Preferably, the first and second matrices are sandwiched between a backing and a top impermeable laminates wherein at least one of the backing and top laminate is transparent or translucent.

In accordance with a specific embodiment of the invention, the strip is configured for the detection of enzyme activity in a fluid sample. In accordance with this embodiment, the detection composition comprises a chromogenic substrate reagent system specific to the enzyme in assay. The chromogenic substrate reagent system may comprise a chromogenic enzyme substrate, such as an indoxyl containing substrate, which yields a colored product upon exposure to the enzyme. Alternatively, the chromogenic substrate reagent system may comprise a mixture of an enzyme substrate and a chromogenic reagent wherein said chromogenic reagent, in the presence of enzymatic reaction between the enzyme and the enzyme substrate, yields a detectable colored product. Preferably, the components of the chromogenic substrate reagent system are soluble in the sample fluid while the colored product is insoluble in the sample fluid.

A second aspect of the invention is a method for determining an analyte in a fluid sample comprising the steps of: providing the novel test strip of the invention as defined above; exposing the test strip to the fluid sample; and observing appearance of a distinct change, preferably a color change, at the interface between the two matrices, wherein appearance of a distinct change indicates presence of the analyte in the fluid sample.

Yet a third aspect of the invention is a method for fabricating a strip adapted for the detection of an analyte in a fluid sample, the method comprising the steps of: selecting a detection composition for the detection of said analyte, said detection composition is selected so as to produce at least one detectable product upon exposure to the analyte; selecting a first and a second flow matrices of different characteristics so as retain the at least one detectable product at an interface between said first and second matrices when the sample travels from the first matrix to the second matrix; arranging the first and second matrices in a sequential order on a non-absorbing support so as to form an interface therebetween; and providing the first matrix with a predetermined amount of the detection composition.

BRIEF DESCRIPTION OF THE DRAWINGS

The present invention will be understood and appreciated more fully from the following detailed description taken in conjunction with the drawings in which.

DETAILED DESCRIPTION OF THE PREFERRED EMBODIMENT

The present invention provides a novel strip for lateral flow assays for the determination of an analyte in fluid samples, including human, animal or man-made samples. The strips of the invention can be used for qualitative, semi-quantitative or quantitative determination. The invention further provides methods for fabricating and using the strip.

The strip of the invention is suitable for, but is not limited to, the detection of enzyme activity in sample fluids and more particularly in bodily fluids. Detection of enzyme activity is useful in the analysis of a biological or chemical sample such as whole organisms, cells or cell extracts, biological fluids, or chemical mixtures. In particular, enzyme levels in bodily fluids are indicative of health condition. Evaluating activity of certain enzymes may provide information about metabolism, disease state and the identity of viral and bacterial pathogens The strip of the invention comprises at least two sequentially ordered solid flow matrices of different characteristics wherein all the detection reactants are movably bound to the first matrix and wherein the capture zone is formed at the interface between two flow matrices. No immobilized reagents are provided on either the first or the second matrices. The term "flow matrix" as used throughout the application refers to any liquid permeable transport solid material that allows for liquid flow therethrough, including materials such as nitrocellulose, nylon, rayon, cellulose, paper, glass fiber and silica or any other porous, fibrous, bibulous or non-bibulous materials. The flow matrix is preferably configured as a substantially planar elongated strip. The flow matrix material can be pretreated or modified as needed.

Figure 1:
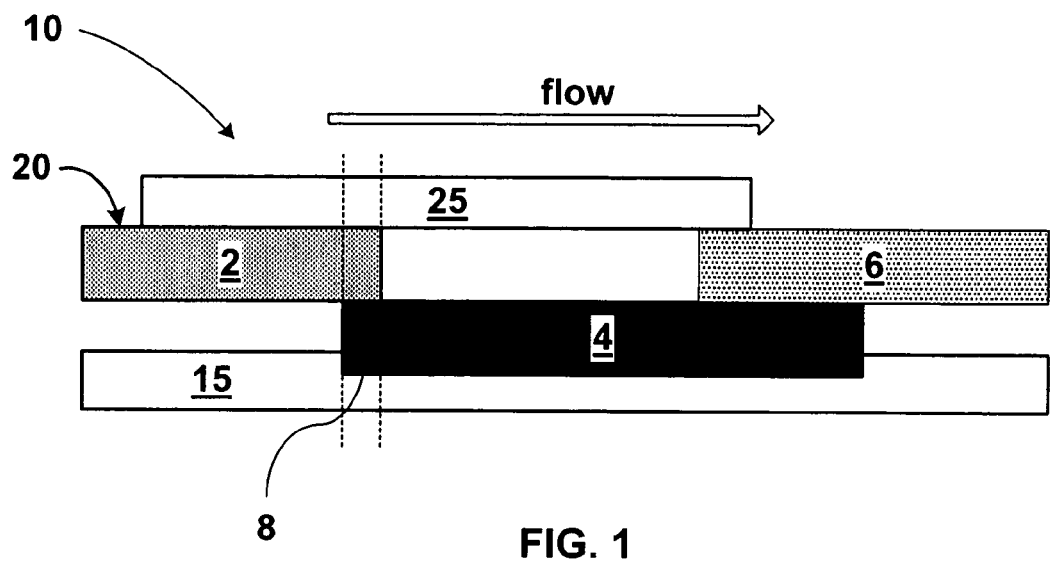
FIGS. 1 and 2 are an exploded side view and a top view, respectively, of a lateral flow strip constructed in accordance with a preferred embodiment of the invention.
Figures 2, 3:
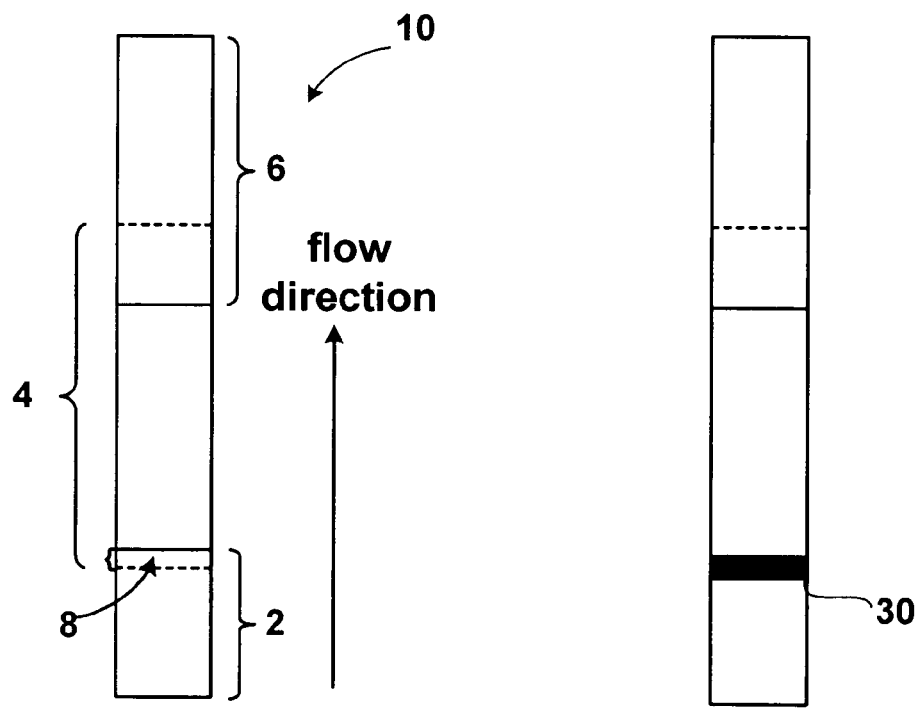
FIG. 3 is a schematic illustration of a positive signal obtained on a lateral flow strip of the invention.

Referring to FIGS. 1 and 2 there is shown a strip of the invention, generally designated 10. Strip 10 comprises two flow matrices, a sample receiving solid matrix 2 and a reaction solid matrix 4 sequentially ordered on backing layer 15 so as to form an interface zone 8 of about 1-5 mm length where matrices 2 and 4 overlap. Interface overlapping zone 8 is the signal zone where a detectable change, typically a color change, appears upon positive determination. Matrices 2 and 4 are selected to have different porosity and consequently different permeation rates. In particular, the matrices are selected so that the permeation rate through matrix 2 is higher than the permeation rate through matrix 4. Matrix 2 may be a glass fiber (GF), a filter paper or any other known in the art filtration or mesh medium of relatively large pore size, preferably a fibrous material. Matrix 4 is preferably, but is not limited to, a nitrocellulose (NC) or a nylon membrane. Preferably, the pore size of membrane 4 is in the range of from about 0.22 μm to about 15 μm. A specific membrane 4 is selected according to the specific assay for which the strip is designed and to the detectable product thereof so as retain the detectable product at interface 8. The strip further comprises an absorbent pad 6 to ensure continuous flow of the sample and a top laminate 25. Top laminate 25 is configured to fully cover membrane 4 and to partially cover membrane 2 and absorbent pad 6, leaving a portion 20 of membrane 2 uncovered where the sample is to be applied and most of pad 6 exposed. Absorbent pad 6 is made of a bibulous material, such as a cellulose or filter paper, so that liquid is drawn through matrices 2 and 4 and accumulates in absorbing pad 6. The size and shape of pad 6 is chosen according to the volume of liquid to be used in the assay. Typical materials for the pad 6 include, but are not limited to, cellulose and filter paper. Back and top laminate 15 and 25 are non-absorbing films. Preferably, both films 15 and 25 are transparent or translucent films, allowing viewing the signal from both sides of the strip. However, using a white film on one side and a transparent film on the other side can increase the contrast of the signal zone in certain applications. For ease of fabrication laminates 15 and 25 are preferably one-side adhesive plastic films protected by a release liner. In practice, strip 10 is assembled by placing laminate 15 with its adhesive side upward, peeling the release liner and placing matrices 2, 4 and 6 on liner 15 as illustrated in FIG. 1. To complete the assembly laminate 25 is placed on top with its adhesive side downward.

An analyte-specific detection composition is movably deposited on sample receiving matrix 2. The detection composition contains reagents which, in the presence of the analyte, produce at least one detectable product that accumulates at interface 8 between matrices 2 and 4. The detection composition may further comprise a surfactant for enhancing the signal intensity. In an enzymatic assay, for example a sialidase assay, the detection composition may contain a chromogenic enzyme substrate, such as for example 5-bromo-4-chloro-3-indolyl-α-D-N-acetylneuraminic acid (BCIN) that in presence of sialidase yields indoxyl, and a color-developing reagent such a tetrazolium salt which reacts with the indoxyl to produce the intensely colored insoluble indigo and formazan dyes. In other examples of enzymatic assays, the detection composition may comprise a mixture of an enzyme substrate and a chromogenic reagent that participates in the enzymatic reaction to yield a detectable product. Such a chromogenic reagent may be for example an electron acceptor or an electron donor participating in the enzymatic electron transfer chain. For example, dehydrogenase enzymes may be detected using a detection composition comprising a dehydrogenase substrate and a chromogenic electron acceptor such as a tetrazolium salt. Peroxidase enzymes may be detected using a detection composition comprising a peroxidase substrate and a chromogenic electron donor, such as tetramethylbenzidine (TMB). Generally, implementation of enzymatic assays in the present device may be achieved by selecting detection compositions equivalent to those used in enzyme histochemistry, namely compositions that include a substrate for the enzymes of interest and reagents that yield insoluble colored or otherwise detectable precipitates in the presence of the enzymatic reaction.

With right selection of matrices 2 and 4, the colored precipitate particles are retained and concentrated at the interface between the two matrices to produce a distinct signal.

The locations of the various detection components on the flow matrix 2 may fully or partially overlap each other or may comprise separate zones. Similarly, the sample application zone may overlap the zone/s impregnated with the detection components or may be a separate zone. It will be realized that the specific locations of the various zones on matrix 2 may vary providing that all of the sample components and all of the detection components are fully mixed and dissolved within the sample fluid as it travels along matrix 2 and before it reaches matrix 4, so as to allow sufficient interaction time. For simplicity and ease of fabrication, it is convenient to fully impregnate matrix 2 with all of the detection components. Thus, if the mixture of all the detecting components is stable in solution, matrix 2 may be soaked in such a solution for a predetermined time and let to dry. Alternatively, if the solution is not stable, matrix 2 may be fully or partially soaked in a solution which contains only those components that are stable together. The remaining components may be loaded on the dry matrix either on the zone pre-impregnated with the dry form of the solution components or on a free, non-impregnated zone. Yet another alternative is to load one or more of the components onto matrix 2 immediately before or after or substantially at the same time of the sample loading.

It should be noted that in accordance with the present invention, the detection composition contains no preformed labeling particles, such as latex or colloidal gold particles. Such inert particles, bound to a member of a biospecific pair, are well known in the art as labeling means for generating a signal by forming a complex with a second member of the biospecific pair. According to the present invention, a positive signal is generated by the formation of a new product having a detectable property, for example a distinct color, which was not present on the strip before and whose formation requires the analyte presence. Thus, unlike the case where detection is based on capturing pre-deposited colored particles, the signal of the present invention is based on the formation of a new product having a new distinct detectable property. This detectable product, formed upon chemical reaction between the detecting components and the analyte, namely upon cleavage and formation of chemical bonds, concentrates at the interface between two matrices, thus enhancing the signal. Preferably, the detectable product is insoluble in the sample fluid so as to form precipitate particles that are retained by the second, less permeable, matrix while the detection composition contains only reagents that are completely dissolvable in the elution fluid.

To perform a test, a sample and an elution agent, typically a running buffer, are loaded on exposed end 20 of pad 2. Typically, the sample is an aqueous solution or a biological fluid. The sample may be added to the running buffer beforehand to be loaded as one solution or alternatively, the running buffer may be loaded after the sample is spotted. As the sample solution moves along the strip, the pre-deposited detecting components are re-dissolved in the solution to be mixed and react with the sample components as the sample liquid travels along the strip. Thus, in the enzymatic example given above, if enzyme is present in the sample the chromogenic substrate cleaves to yield the chromogenic intermediate which further reacts with the color-developing reagent to yield the intensely colored products. The colored product accumulates at the overlapping interface 8 between the two matrices to give rise to a clear distinguished signal line. Referring to FIG. 3, a positive result is indicated by the appearance of a distinguished line 30 at signal zone 8 while a negative result is indicated by absence of such a line at the signal zone.

The lateral flow strip of the invention may be used in a qualitative manner to give positive/negative answer corresponding to the presence or absence of analyte in a test sample. In accordance with this embodiment, the strip may be incorporated into a lateral flow device provided with a receiving port for loading the sample and at least one transparent window at the signal zone, thus providing a simple self-contained detecting device which requires no additional equipment. A reference may be added with a calibrated color intensity scale to make a semi-quantitative measurement by matching the signal intensity to the calibrated scale. Alternatively, the strip may be read by an instrument, such as, but not limited to, spectrophotometer, scanner, densitometer, reader, camera, to give a quantitative result. Since, as mentioned before, the signal can be viewed from both sides of the strip, it allows for measuring both the absorbance and the reflectance of the signal.

The following detailed examples are given for the sake of illustration only and are not intended to limit the invention to what is described therein.

Example 1

Sialidase Test Strip

A sialidase test strip for the detection of sialidase activity in a fluid sample was constructed in accordance with the present invention, as described below. The assay is based on the hydrolysis of the chromogenic sialidase substrate 5-bromo-4-chloro-3-indolyl-α-D-N-acetylneuraminic acid (BCIN) in the presence of sialidase to yield indoxyl and the further reaction of the so produced indoxyl with nitro blue tetrazolium (NBT) to produce indigo and formazan which accumulate at the interface between the two matrices. The chemical structures of BCIN and NBT as well as a detailed reaction scheme of the assay reactions appear in a co-pending application titled "Dry Format Sialidase Assay", filed on the same date and assigned to the same assignee of the present invention, the full content of which is incorporated herein by reference. Various samples were tested with the strip including vaginal swab samples for the detection of Bacterial Vaginosis (BV).

A. Preparation of NBT-Impregnated Sample Pads

Glass fiber filters (Millipore, GFCP0010000, 10 mm×10 cm) were soaked in NBT solution for 30 minutes in the dark at room temperature. The soaked glass fiber filters were placed on a blotting paper to remove excess fluids and then transferred to drying oven for 15 minutes at 50° C. The dried NBT-impregnated glass fiber filters (sample pads) were stored dried and dark in a dry room (RH 5-10%) at room temperature.

B. Card Assembly

Figure 4:
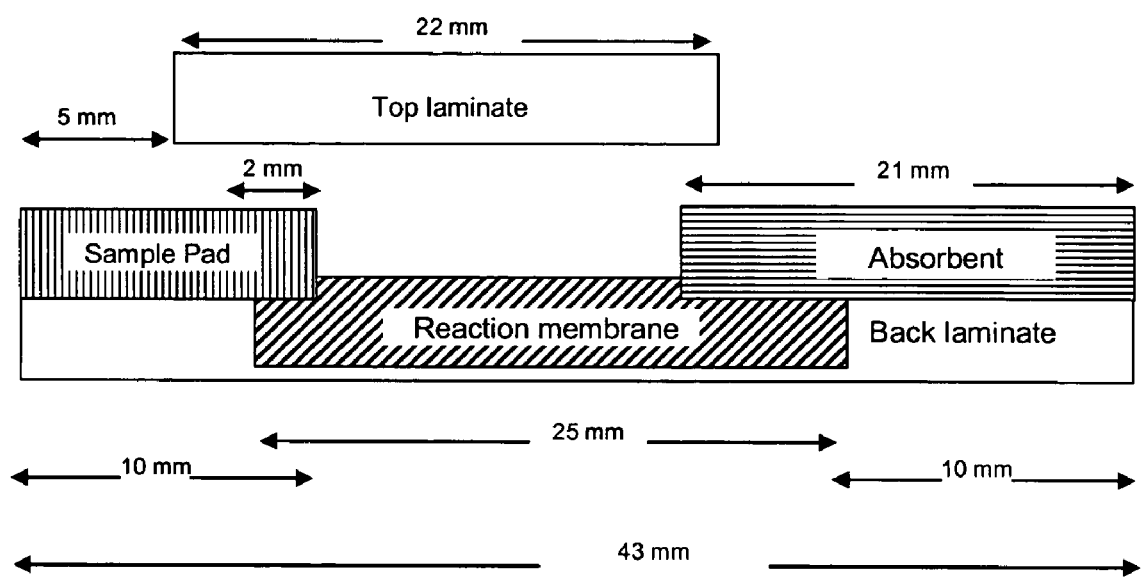
FIG. 4 is an exploded-view construction scheme of the strips used in examples 1 to 3 of the specification, specifying the dimensions and relative positions of the different strip layers.

A test card was assembled according to the following procedure and in accordance with FIG. 4 which specifies the exact longitudinal dimensions and position of each of the card components. Following preparation, the card was trimmed to obtain a plurality of strips for sialidase assay.

1. A 43×250 mm piece of clear plastic film with a release liner protected adhesive, serving as the back laminate, designated 15 in FIG. 2, (ARcare 8876, Adhesives Research, Limerick, Ireland) was placed on top of a worktable. The release liner was peeled to expose the adhesive side of the tape.
2. The reaction membrane (Nitrocellulose HF18004, Millipore, SA3J154101, 25×300 mm or Biodyne B, PALL, BNBZF3RT, 25×300 mm or Biodyne PLUS, PALL, ZNXG3R, 25×300 mm) was attached on top of the adhesive side of the back cover, 8 mm from the lower end.
3. The NBT-impregnated sample pad (prepared as in section A) was attached on top of the lower side of the back cover with 2 mm overlap on top of the reaction membrane.
4. The absorbent pad (Gel blotting paper, S&S, GB003, 21×300 mm) was placed on top of the upper side of the back cover with a 12 mm overlap on top of the reaction membrane.

5. The release liner of top laminate film (ARcare 7759, Adhesives Research, Limerick, Ireland) was peeled to expose the adhesive side and the film was attached, with the adhesive facing done, on top of the reaction membrane, with overlaps on top of the sample pad and absorbent pad.

The card was cured over-night in a dry room (RH 5-10%) at room temperature in the dark. Following curing, the card was trimmed to 4 mm width strips using an automated die cutter.

C. Impregnation of BCIN on the Strip Sample Pads

1 µl of BCIN (5-bromo-4-chloro-3-indolyl-□-D-N-acetyl-neuraminic acid) solution was added on top of the sample pad and allowed to dry for 15 minutes at 37° C.

D. Running of Tests with Sialidase Test Strips

D1. Bacterial and Purified Sialidase Samples

The strips constructed as described in section B above, were tested for sialidase activity with samples of sialidase producing bacteria: *Bacteroides fragilis*, sialidase negative bacteria: *Lactobacillus plantarum* and with purified sialidase.

Figure 5:
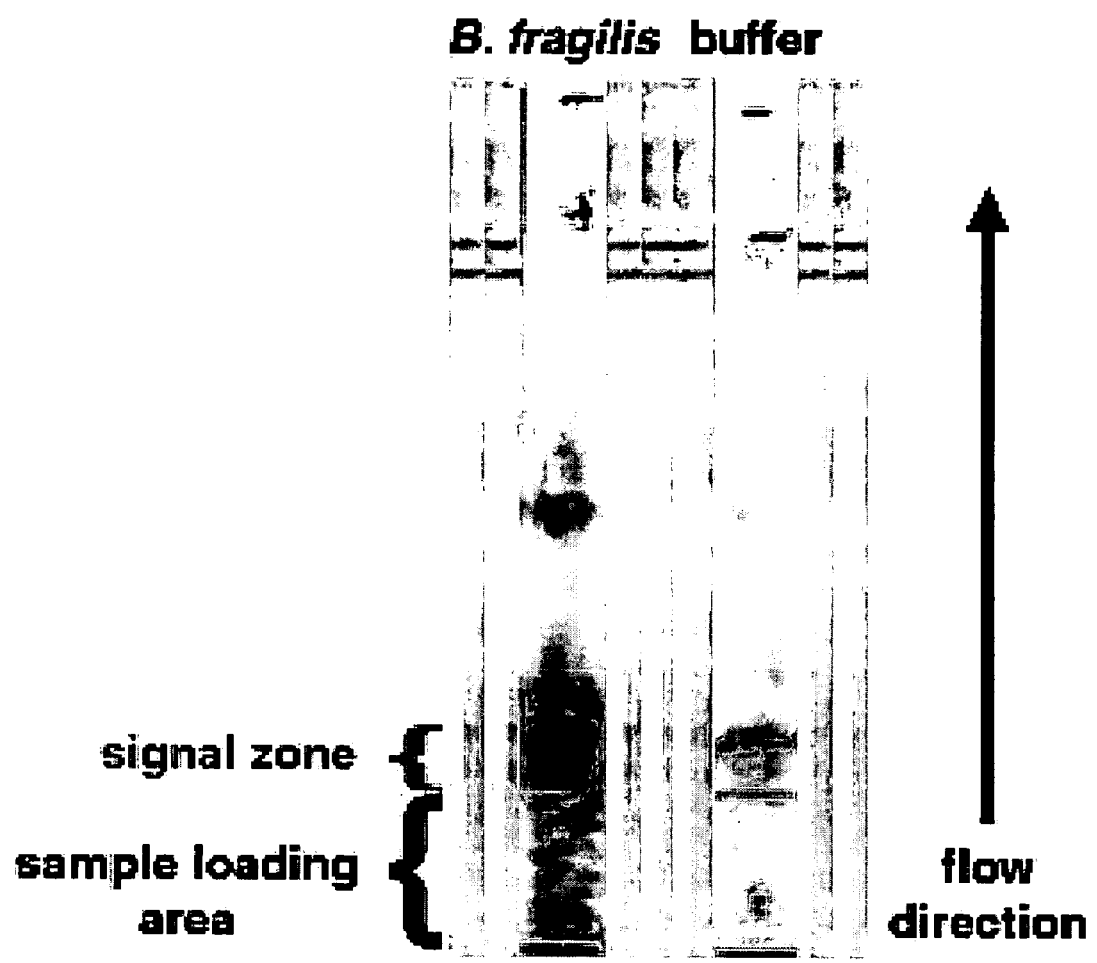
FIG. 5 shows exemplary results obtained with a lateral flow strip of the invention configured for the detection of sialidase; the left strip shows results obtained with a sample of *B. fragilis*; the right strip shows a control run with a running buffer; the strips were scanned after 10 minutes incubation.

To start a test, 25 µl of sample was loaded onto the sample pad of the strip. The signal of positive sialidase reaction, a brown-purple color, was accumulated at the interface between the two different matrices (sample pad and the reaction membrane), namely the signal zone. Negative control (where no sialidase present) showed a yellow background at the signal zone. For each test the signal appearance time was recorded. The strips were observed up to 30 minutes. FIG. 5 shows exemplary results obtained with a sample of *Bacteroides fragilis* (left strip) and with a running buffer (right strip) as a negative control.

The color change at the signal zone could be observed visually and was assigned "+" values corresponding to intensity as estimated by eye (see Table 1). Alternatively or in addition, the color can be detected and measured by an electro-optical instrument. The signal appearance time from the loading of the sample to the test strip and the intensity of the signal at 10 minutes are summarized in following Table 1.

TABLE 1 results obtained by the sialidase test strip

| Sample (25 µl) | Time of signal appearance (minutes) | Signal intensity after 10 minutes* |
|---|---|---|
| *B. fragilis* $5*10^4$ cells | 2 | ++++ |
| *B. fragilis* $2.5*10^4$ cells | 3 | +++ |
| *B. fragilis* $10^4$ cells | 6 | ++ |
| *B. fragilis* $5*10^3$ cells | 8 | + |
| *B. fragilis* $2.5*10^3$ cells | — | − |
| *B. fragilis* $10^3$ cells | — | − |
| *L. plantarum* $5*10^5$ cells | — | − |
| Purified sialidase 5 units | 1 | ++++ |
| Purified sialidase 1 units | 1 | ++++ |
| Buffer | — | − |

*Relative signal intensity: Very strong (++++), strong (+++), medium (++), weak (+) and no signal (−).

D2. Clinical Samples (Vaginal Swabs)

47 clinical samples were tested to test the clinical relevance of the Sialidase test strip for the diagnosis of Bacterial Vaginosis BV. Vaginal discharge samples were obtained from volunteers at the Genitourinary Infections unit of the Wolfson Medical Center, Holon, Israel. Vaginal discharges were collected by a physician using a sterile swab (552C, Copan, Italia). The swab heads (tips) were placed in 2 ml screw-cap tubes and kept at 4° C. until use. The vaginal swabs were washed by adding 300 µl of running buffer in to the tube and by vortexing for 1 minute to elute the secretions from the swab and to achieve a homogenous sample. For each vaginal swab a diagnosis for BV was done using Gram staining and Nugent scoring (RP Nugent et al. Reliability of Diagnosing Bacterial Vaginosis Is Improved by a Standardized Method of Gram Stain Interpretation (J. Clin. Microbiol., 29: 297-301 (1999)). From the 300 µl swab wash, 25 µl were taken for the test. The test was done as described above for culture samples.

Table 2 summarizes the result of 47 vaginal swabs washes that were diagnosed for BV and tested with the Sialidase test strip.

TABLE 2 results obtained by sialidase test strip for of 47 vaginal swabs diagnosed for BV by Nugent score

| | | BV (Nugent score) | |
|---|---|---|---|
| | N = 47 | Positive | Negative |
| Sialidase test strip | Positive | 22 | 0 |
| | Negative | 0 | 25 |
| | Total | 22 | 25 |

The sensitivity and specificity of the Sialidase test strip are 100%. The results summarized in Table 1 and 2 clearly demonstrate that the proposed sialidase test strip could be used for the diagnosis of BV Materials and Preparation of Solutions for Sialidase Assay:

NBT solution 2 mg/ml NBT (Nitro blue tetrazolium chloride, N-8100 Biosynth AG, Switzerland), 5% sucrose (5553810, Frutarom, Haifa, Israel), 0.1% $MgCl_2$ (1200310, Merck, Darmstadt, Germany) in 50 mM MES (M-8250, Sigma-Aldrich, Rehovoth, Israel) buffer pH 6.0; NBT solution with Surfynol-440 2 mg/ml NBT (Nitro blue tetrazolium chloride, N-8100 Biosynth AG, Switzerland), 5% sucrose (5553810, Frutarom, Haifa, Israel), 0.1% $MgCl_2$ (1200310, Merck, Darmstadt, Germany), 0.5% surfynol-440 (2,4,7,9 tetramethyl-5-decyne-4,7-diol ethoxylate 1.75EO/OH, Aldrich, 461180) in 50 mM MES (M-8250, Sigma-Aldrich, Rehovoth, Israel) buffer pH 6.0; BCIN Solution 35.3 mg BCIN (5-Bromo-4-chloro-3-indolyl-α-D-N-acetyl-neuraminic acid sodium salt, B4666, Sigma) in 1 ml double distilled water; Running Buffer 0.5% PEG (PolyEthyleneGlycol-15000, Merck, 819003), 0.5% BSA (01200050, Seracare, Calif., USA), 0.1% Tween 20 (Sigma, P-5927), 0.1% $MgCl_2$ (Merck 1200310) in TBS (Tris buffer saline) pH 7.8.

Bacterial Cultures

Sialidase producing bacteria: Culture of *Bacteroides fragilis* (ATCC #23745) $10^7$ cfu/ml. 25 µl of sample was prepared by dilutions of the culture in running buffer to the following number of cells: $5*10^4$, $2.5*10^4$ $10^4$ and $5*10^3$. Sialidase negative bacteria: Culture of *Lactobacillus plantarum* (ATCC #14917) $10^8$ cfu/ml. 25 µl of sample with $5*10^5$ cells was prepared by dilution of the culture in running buffer. Purified Sialidase Purified recombinant bacterial sialidase from *Clostridium perfringens* (P0720L, Neuraminidase), was obtained from New England Biolabs, MA, USA). 25 µl samples were prepared by dilutions of the purified sialidase in running buffer to the following levels: 5 units and 1 unit per sample.

Example 2

Alkaline Phosphatase Test Strip

A test strip for the detection of alkaline phosphatase (AP) activity in a fluid sample was constructed similarly to the manner described above in Example 1. The assay is based on the hydrolysis of the chromogenic phosphatase substrate 5-bromo-4-chloro-3-indolyl phosphate (BCIP) in the presence of AP to yield indoxyl and the further reaction of the so produced indoxyl with nitro blue tetrazolium (NBT) to produce indigo and formazan which accumulate at the interface between the two matrices. The main difference between the present and the above strip examples is that in the present example the sample receiving matrix was soaked in a solution containing both the chromogenic substrate BCIP and the color-developing reagent NBT.

A. Preparation of BCIP-NBT-Impregnated Sample Pads

Glass fiber filters (Millipore, GFCP0010000, 10 mm×10 cm) are soaked in BCIP-NBT solution (0.2 mg/ml BCIP+0.3 mg/ml NBT in 0.1 M Tris buffer pH 9.6) for 30 minutes in the dark at room temperature. The glass fiber filters are transferred to drying oven and are dried for 15 minutes at 50° C. The BCIP-NBT-impregnated glass fiber filters (sample pads) are stored dried and dark in a dry room (RH 5-10%) at room temperature.

B. Card Assembly and Strip Trimming

A test card was assembled according to the following procedure and in accordance with FIG. 4, which specifies the exact longitudinal dimensions and position of each of the card components. Following preparation, the card was trimmed to form a plurality of strips for AP assay.
1. A clear plastic film with a release liner protected adhesive, namely the back cover, 43×250 mm piece (ARcare 8876, Adhesives Research, Limerick, Ireland) was placed on top of a worktable. The release liner was peeled to expose the adhesive side of the tape.
2. The reaction membrane (Nitrocellulose HF18004, Millipore, SA3J154101, 25×300 mm was attached on top of the adhesive side of the back cover, 8 mm from the lower end.
3. The BCIP-NBT impregnated sample pad was attached on top of the lower side of the back cover with 2 mm overlap on top of the reaction membrane.
4. The absorbent pad (Gel blotting paper, S&S, GB003, 21×300 mm) was placed on top of the upper side of the back cover with a 12 mm overlap on top of the reaction membrane.
5. The release liner of top laminate film (ARcare 7759, Adhesives Research, Limerick, Ireland) was peeled to expose the adhesive side and the film was attached, with the adhesive facing done, on top of the reaction membrane, with overlaps on top of the sample pad and absorbent pad.

C. Test for Alkaline Phosphatase (AP) Activity with Anti-Digoxigenin AP
   a. 25 µl samples were prepared by dilutions of anti-Digoxigenin AP (Roche 1093274 0.75 unit/µl) in TBS (Tris buffer saline) pH 7.8 to the following levels: 0.0375 units/test, 0.00375 units/test and 0.000375 units/test.
   b. 25 µl of sample was loaded onto the sample pad of the strip.

Figure 6:
FIG. 6 shows exemplary results obtained with a lateral flow strip of the invention configured for the detection of alkaline phosphatase (AP)

Results:

The test results are shown in FIG. 6. The signal of positive reaction, a brown-purple color, was accumulated at the interface between the two different matrices (sample pad and the reaction membrane), namely the signal zone. Negative control (where no anti-Digoxigenin AP was present) didn't show any signal.

All positive signals appeared within 3 minutes.

Example 3

Peroxidase Test Strip

A test strip for the detection of peroxidase (POD) activity in a fluid sample was constructed similarly to the manner described above in Examples 1 and 2. However in this example, the sample receiving matrix was not impregnated with the detection reagents but was assembled into the strip in its clean untreated form. A commercially available solution of chromogenic peroxidase substrate mixture, with tetramethylbenzidine (TMB) as the chromogen, was loaded onto the strip just before loading the sample. In the presence of peroxidase, the TMB substrate mixture yields a colored product. Two different TMB peroxidase substrate mixtures, Sigma T0565 and Pierce #34028, were tested. The sigma substrate is reported to yield insoluble product and is recommended for membrane applications. The Pierce substrate yields soluble product substrate and is intended for use in ELISA.

A. Running Buffer 0.5% PEG (PolyEthyleneGlycol-15000, Merck, 819003), 0.5% BSA (01200050, Seracare, Calif., USA), 0.1% Tween 20 (Sigma, P-5927), 0.1% $MgCl_2$ (Merck 1200310) in TBS (Tris buffer saline) pH 7.8.

B. Card Assembly and Strip Trimming

A test card was assembled according to the following procedure and in accordance with FIG. 4, which specifies the exact longitudinal dimensions and position of each of the card components. Following preparation, the card was trimmed to form a plurality of strips for POD assay.
1. A clear plastic film with a release liner protected adhesive, namely the back cover, 43×250 mm piece (ARcare 8876, Adhesives Research, Limerick, Ireland) was placed on top of a worktable. The release liner was peeled to expose the adhesive side of the tape.
2. The reaction membrane (Nitrocellulose HF18004, Millipore, SA3J154101, 25×300 mm was attached on top of the adhesive side of the back cover, 8 mm from the lower end.
3. The sample pad (Glass fiber filter, Millipore, GFCP0010000, 10 mm×10 cm) was attached on top of the lower side of the back cover with 2 mm overlap on top of the reaction membrane.
4. The absorbent pad (Gel blotting paper, S&S, GB003, 21×300 mm) was placed on top of the upper side of the back cover with a 12 mm overlap on top of the reaction membrane.
5. The release liner of top laminate film (ARcare 7759, Adhesives Research, Limerick, Ireland) was peeled to expose the adhesive side and the film was attached, with the adhesive facing done, on top of the reaction membrane, with overlaps on top of the sample pad and absorbent pad.

C. Test for Peroxidase (POD) Activity with Anti-Digoxigenin POD
   a. 25 µl samples were prepared by dilutions of anti-Digoxigenin POD (Roche 1207733 0.15 unit/µl) in running buffer to the following levels: 7.5 units/test, 0.75 units/test and 0.075 units/test.
   b. 5 µl of tetramethylbenzidine (TMB) substrate mixture (Sigma T0565, or Pierce #34028) was placed on the sample pad of the strip.
   c. The 25 µl of sample was loaded on top of the sample pad.

Figure 7:
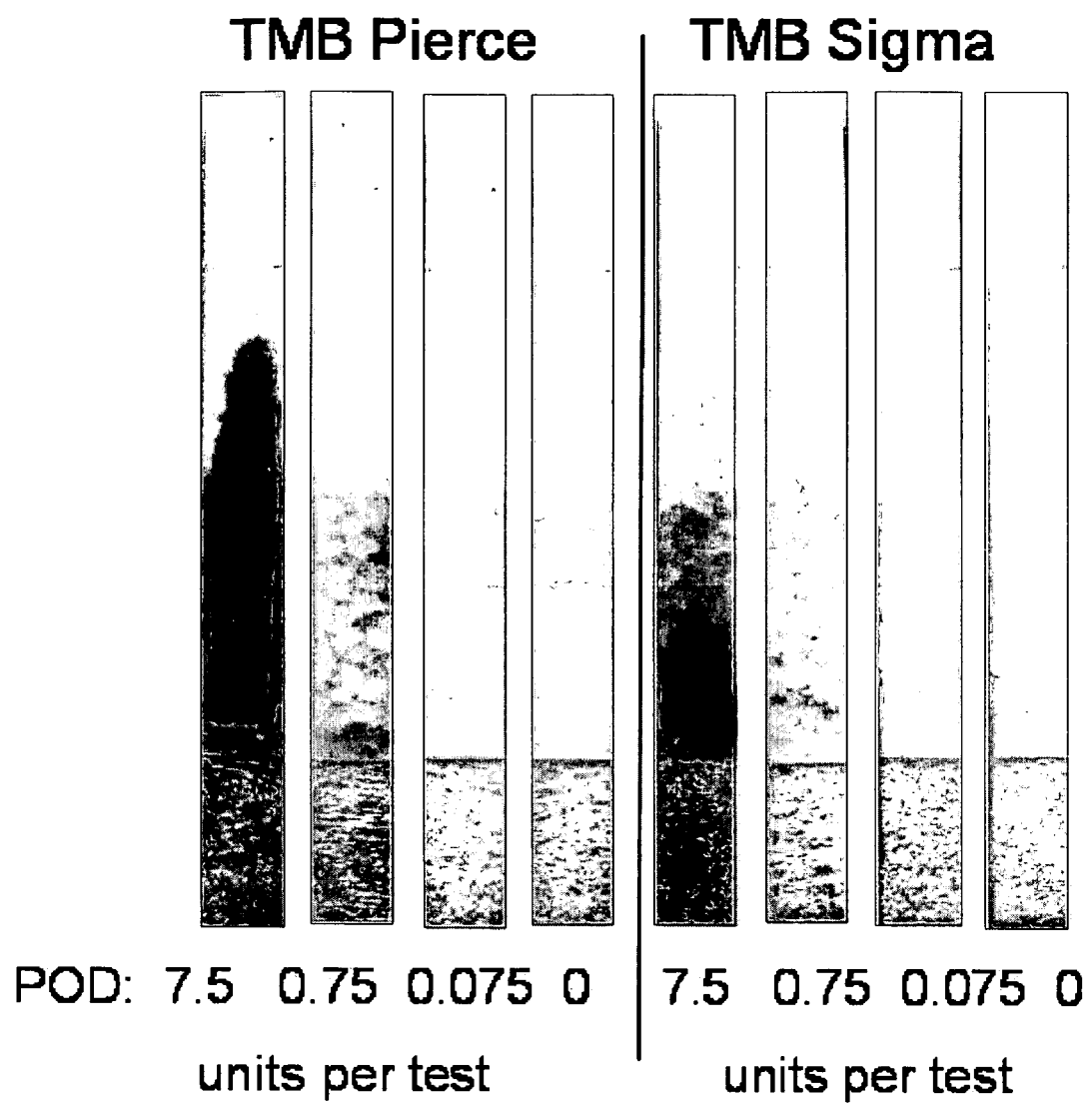
FIG. 7 shows exemplary results obtained with a lateral flow strip of the invention configured for the detection of peroxidase (POD).

Results:

FIG. 7 shows the results obtained with the Sigma substrate and the Pierce substrate. The signal of positive reaction, a blue-purple color, was accumulated at the sample pad and at the interface between the two different matrices (sample pad and the reaction membrane), namely the signal zone. Negative control (where no anti-Digoxigenin POD was present) didn't show any signal. All positive signals appeared within 3 minutes.

It will be appreciated by persons skilled in the art that the present invention is not limited to what has been particularly shown and described hereinabove. Rather the scope of the present invention is defined only by the claims which follow.

The invention claimed is:

1. A test strip configured for the detection of an analyte in a fluid sample, the strip comprising a first flow matrix and a second flow matrix sequentially arranged to form an interface therebetween, said first flow matrix comprises a detection composition movably bound thereto;
   wherein the detection composition is selected to chemically react with said analyte to yield at least one detectable product;
   wherein said at least one detectable product is a precipitate that does not comprise the analyte; and
   wherein the first and second flow matrices are selected so as to accumulate said at least one detectable product at said interface when the fluid sample travels from the first flow matrix to the second flow matrix.

2. The strip of claim 1 wherein at least one component of said detection composition is deposited on said first matrix in a re-dissolvable dry form.

3. The strip of claim 1 wherein said first matrix is of higher porosity than said second matrix.

4. The strip of claim 1 wherein the transport rate of said at least one detectable product through the first matrix is higher than the transport rate of said at least one detectable product through the second matrix.

5. The strip of claim 1 wherein the first matrix is a glass fiber or a filter paper and wherein the second matrix is a nitrocellulose or a nylon membrane.

6. The strip of claim 1 wherein said analyte is soluble.

7. The strip of claim 1 wherein said detection composition is dissolvable in the sample fluid.

8. The strip of claim 1 wherein said first and second matrices are sandwiched between a backing and a top impermeable laminates.

9. The strip of claim 8 wherein at least one of said backing and top laminate is transparent or translucent.

10. The strip of claim 1 wherein said analyte is an enzyme and wherein said detection composition comprises a chromogenic substrate reagent system specific to said enzyme.

11. A strip for the detection of an enzyme in a fluid sample, the strip comprising a first matrix and a second matrix sequentially arranged on a non-absorbing solid support forming a junction therebetween,
   wherein the first matrix is provided with a movably bound enzyme detection composition, which upon exposure to said enzyme produces at least one insoluble detectable product, said
   detectable product does not comprise said enzyme; and
   wherein said first and second matrices are selected so as to accumulate said at least one detectable product at said junction when the fluid sample travels from the first flow matrix to the second flow matrix.

12. The strip of claim 11 wherein said enzyme detection composition comprises a chromogenic substrate of said enzyme.

13. The strip of claim 12 wherein said enzyme detection composition further comprises a color intensifier.

14. The strip of claim 12 wherein said substrate comprises an indoxyl group.

15. The strip of claim 14 wherein the enzyme detection composition further comprises a tetrazolium salt.

16. The strip of claim 11 wherein said enzyme detection composition comprises a substrate of said enzyme and a chromogenic reagent, wherein said chromogenic reagent yields a detectable colored product in the presence of enzymatic reaction between the enzyme and the enzyme substrate.

17. The strip of claim 16 wherein said chromogen reagent is an electron donor or an electron acceptor.

18. A method for detecting an analyte in a fluid sample, the method comprising the steps of:
   providing a test strip as defined in claim 1;
   loading a fluid sample onto the first flow matrix of said test strip; and
   observing appearance of a color change at the interface between the first and second flow matrices;
   wherein appearance of a distinguished color change indicates presence of the analyte in said fluid sample.

19. A test strip configured for the detection of a soluble analyte in a fluid sample, the strip comprising a first flow matrix and a second flow matrix sequentially arranged to form an interface therebetween, said first flow matrix comprises a detection composition movably bound thereto, wherein the detection composition is selected to react with said analyte to yield at least one insoluble detectable product which does not comprise said analyte, and wherein the first and second solid matrices are selected so as to accumulate said at least one detectable product at said interface when the fluid sample travels from the first flow matrix to the second flow matrix.

* * * * *